United States Patent
Sainz de Cea et al.

(10) Patent No.: US 11,308,619 B2
(45) Date of Patent: Apr. 19, 2022

(54) EVALUATING A MAMMOGRAM USING A PLURALITY OF PRIOR MAMMOGRAMS AND DEEP LEARNING ALGORITHMS

(71) Applicant: International Business Machines Corporation, Armonk, NY (US)

(72) Inventors: Maria Victoria Sainz de Cea, Somerville, MA (US); David Richmond, Newton, MA (US); Chao Song, Chicago, IL (US)

(73) Assignee: International Business Machines Corporation, Armonk, NY (US)

( * ) Notice: Subject to any disclaimer, the term of this patent is extended or adjusted under 35 U.S.C. 154(b) by 0 days.

(21) Appl. No.: 16/932,140

(22) Filed: Jul. 17, 2020

(65) Prior Publication Data
US 2022/0020151 A1    Jan. 20, 2022

(51) Int. Cl.
*G06K 9/00* (2022.01)
*G06T 7/00* (2017.01)
(Continued)

(52) U.S. Cl.
CPC .......... *G06T 7/0014* (2013.01); *G06K 9/6232* (2013.01); *G06K 9/6256* (2013.01);
(Continued)

(58) Field of Classification Search
CPC ........ G06T 7/0014; G06T 2207/30068; G16H 30/20; G16H 50/70; G06K 9/6232; G06K 9/6256; G06K 9/6267; G06N 3/08
See application file for complete search history.

(56) References Cited

U.S. PATENT DOCUMENTS 10,037,601 B1 * 7/2018 Ben-Ari ............... G06K 9/6226
2005/0207630 A1   9/2005 Chan
(Continued)

FOREIGN PATENT DOCUMENTS

WO    2008157843 A1    12/2008

OTHER PUBLICATIONS

Arefan, D. et al., "Deep learning modeling using normal mammograms for predicting breast cancer risk." 2019 American Association of Physicists in Medicine, 47 (1), pp. 110-118, Jan. 2020.
(Continued)

*Primary Examiner* — Xin Jia
(74) *Attorney, Agent, or Firm* — Alexander G. Jochym (57) ABSTRACT

An approach for training, on a computer, one or more deep learning algorithms with a plurality of mammograms with known outcomes based, at least in part, on using a set of mammograms of each patient in the plurality of mammograms. The approach includes receiving a first set of mammograms of a first patient. The first set of mammograms includes an unevaluated mammogram of the first patient and a set of prior mammograms of the first patient. The approach includes the trained convolutional neural network extracting the set of features from each mammogram of the set of mammograms of the first patient. Furthermore, the approach includes using a second deep learning algorithm of the one or more deep learning algorithms to perform an evaluation of the unevaluated mammogram of the first patient based, at least in part, on the set of prior mammograms of the first patient.

12 Claims, 6 Drawing Sheets

(51) Int. Cl.
G16H 50/70 (2018.01)
G16H 30/20 (2018.01)
G06K 9/62 (2022.01)
G06N 3/08 (2006.01)

(52) U.S. Cl.
CPC ............. *G06K 9/6267* (2013.01); *G06N 3/08* (2013.01); *G16H 30/20* (2018.01); *G16H 50/70* (2018.01); *G06T 2207/30068* (2013.01)

(56) References Cited

U.S. PATENT DOCUMENTS

2019/0172581 A1* 6/2019 Zlotnick ................ G06N 20/00
2019/0220978 A1 7/2019 Moehrle

OTHER PUBLICATIONS

Hayward, J. et al., "Improving screening mammography outcomes through comparison with multiple prior mammograms." American Journal of Roentgenology, 207(4), pp. 918-924, 2016, <https://arxiv.org/abs/1809.08771>.

Kidziński, L. et al., of Stanford University, , "Longitudinal data analysis using matrix completion." (Submitted on Sep. 24, 2018), pp. 1-26, <https://arxiv.org/abs/1809.08771>.

Kooi, T, "Classifying Symmetrical Differences and Temporal Change in Mammography Using Deep Neural Networks." (Submitted on Mar. 22, 2017 (v1), last revised Aug. 1, 2017 (this version, v2)), 18 Pgs, <https://arxiv.org/abs/1703.07715>.

Perek, S, et al., Learning from Longitudinal Mammography Studies. In: Shen D. et al. (eds) Medical Image Computing and Computer Assisted Intervention—MICCAI 2019. Lecture Notes in Computer Science, vol. 11769. Springer, Cham, pp. 712-720, 2019, <http://doi.org/10.1007/97803.030-32226-7_79>.

Santeramo, R; et al., "Longitudinal detection of radiological abnormalities with time-modulated LSTM." Dept. of Biomedical Engineering, Kings College London, (Submitted on Jul. 16, 2018), pp. 1-10, <https://arxiv.org/abs/1807.06144>.

Wang, J. et al., "Discrimination of Breast Cancer with Microcalcifications on Mammography by Deep Learning," Scientific Reports, vol. 6, Article No. 27327, 2016, pp. 1-9.

* cited by examiner

EVALUATING A MAMMOGRAM USING A PLURALITY OF PRIOR MAMMOGRAMS AND DEEP LEARNING ALGORITHMS

BACKGROUND

The present invention relates generally to the field of computer data processing, and more particularly to using multiple prior screening examination images with deep learning algorithms for classifying a screening mammography image.

Implementation of national screening programs have significantly reduced the risk of dying from some forms of cancer due to early disease detection. Reduced risk of death associated with breast cancer, colon cancer, and prostate cancer has been achieved. Improvements in screening examination image evaluations include the use of deep learning algorithms for fine-grained recognition of anomalies and abnormalities using various image classification methods in computer vision for medical imaging have contributed to the improvement in patient outcomes.

A conventional evaluation of a mammogram can be performed by a radiologist or physician. Additionally, trained deep learning algorithms using convolutional neural networks have been demonstrated to evaluate a mammogram image. The evaluation of a mammogram using the trained deep learning algorithms can be used by a physician or radiologist to provide additional data in the radiologist's evaluation of a mammogram. Typically, a radiologist or physician may review the patient's history including prior mammograms to aide in the radiologist's evaluation of a mammogram.

SUMMARY

Embodiments of the present provide a method, a computer program product, and a computer system for training one or more second deep learning algorithms with a plurality of mammograms with known outcomes based, at least in part, on using a set of mammograms from each patient of a plurality of patients from a plurality of mammograms with known outcomes. The method includes one or more computer processors receiving a first set of mammograms of a first patient wherein, the first set of mammograms includes an unevaluated mammogram of the first patient and a set of prior mammograms of the first patient. The method includes one or more computer processors extracting, using a trained convolutional neural network, a set of features from each mammogram of the set of mammograms of the first patient. Furthermore, the method includes one or more computer processors performing an evaluation of the unevaluated mammogram of the first patient using the trained convolutional neural network and a trained deep learning algorithm of the one or more trained deep learning algorithms based, at least in part, on the set of prior mammograms of the first patient.

DETAILED DESCRIPTION

Embodiments of the present invention recognize that the use of deep learning algorithms in the evaluation of mammograms is currently limited to evaluating only a single, most recent mammogram without data from a patient's previous mammograms. Embodiments of the present invention recognize that the evaluation of a single mammogram using deep learning algorithms, as currently practiced, is not as effective as an evaluation performed by an experienced, medical professional. An experienced medical professional or radiologist who specializes reading mammograms can use not only the current mammogram of a patient but also can review the patient's previous mammograms and medical history to provide a more accurate assessment of whether the current mammogram is normal or abnormal than current deep learning algorithms as currently applied to a single, current mammogram.

Embodiments of the present invention provide a method, a computer program, and a computer system using trained deep learning algorithms evaluating a most recent mammogram of a patient based, at least in part, on using one or more prior mammograms of the patient. Embodiments of the present invention use a trained convolutional neural network (CNN) with one of a trained random forester (RF) classifier or a trained modified long-short term memory (LSTM) algorithm for the evaluation of the most recent mammogram of a patient based, at least in part, on one or more prior mammograms of the patient. Embodiments of the present invention improve the effectiveness of current deep learning algorithm evaluations using only a single, most recent mammogram by providing a method of evaluating the most recent mammogram based, in part, on including a number of prior mammograms of the patient in the evaluation that is performed using a trained CNN and a second trained deep learning algorithm that is one of a random forest classifier or a modified LSTM algorithm.

Embodiments of the present invention present not only a method of using multiple prior mammograms of a patient in the evaluation of the most recent mammogram but, also, introduces a method of modifying a traditional LSTM algorithm to include a weighing factor associated with an image quality of each of the prior mammograms and a weighting factor associated with a time elapsed from the most recent mammogram that is being evaluated to each prior mammogram.

The present invention will now be described in detail with reference to the Figures.

Figure 1:
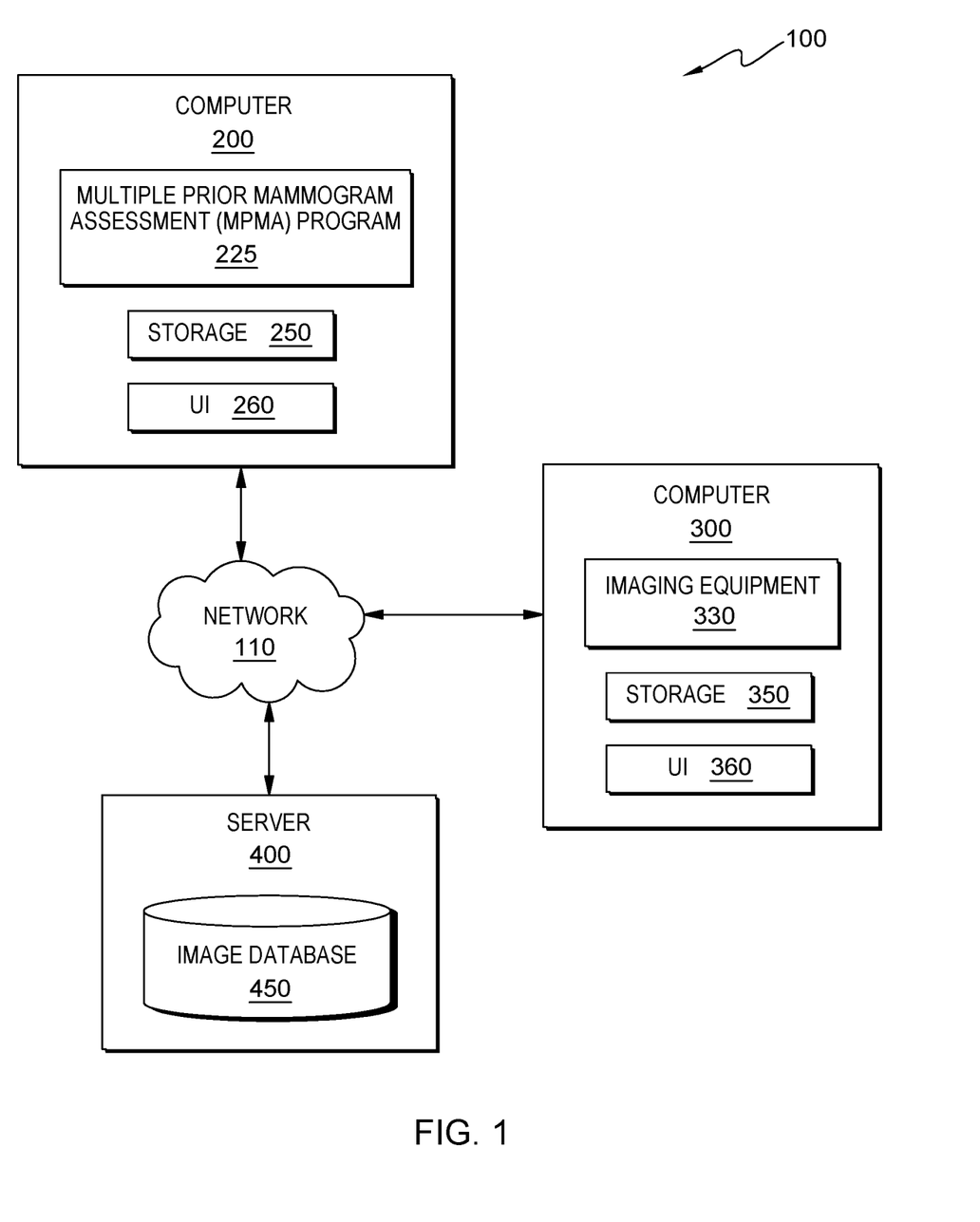
FIG. 1 depicts a functional block diagram of a computing environment suitable for operation of a multiple prior mammogram assessment program, in accordance with at least one embodiment of the invention.

FIG. 1 is a functional block diagram of a computing environment 100 suitable for operation of multiple prior mammogram assessment (MPMA) program 225 in accordance with at least one embodiment of the invention. FIG. 1 provides only an illustration of one implementation and does not imply any limitations with regard to the environments in which different embodiments may be implemented. Implementation of embodiments of the invention may take a variety of forms, and exemplary implementation details are discussed subsequently with reference to the Figures. Many modifications to the depicted environment may be made by those skilled in the art without departing from the scope of the invention as recited by the claims.

Computing environment 100 includes computer 200, computer 300, and server 400 with image database 450 connected over network 110. Network 110 can be, for example, a local area network (LAN), a wide area network (WAN), such as the Internet, a virtual local area network (VLAN), or any combination that can include wired, wireless, or optical connections. In general, network 110 can be any combination of connections and protocols that will support communications between computer 200, computer 300, server 400 and any other computing devices not depicted in FIG. 1.

As depicted, computer 200 is includes MPMA program 225, storage 250, and user interface (UI) 260. In some embodiments, computer 200 can be a desktop computer system, a desktop computer, a laptop computer, a server, a blade server, a tablet computer, a netbook computer, or any other programmable electronic computing device capable of receiving, sending, and processing data, and communicating with features and functions of computer 300 and server 400 and other computing devices not shown within computing environment 100 via network 110. In another embodiment, computer 200 represents a computing system utilizing clustered computers and components (e.g., database server computers, application server computers, etc.) that act as a single pool of seamless resources when accessed within distributed data processing environment 100. Computer 200 may include internal and external hardware components, as depicted in more detail and described in FIG. 5.

MPMA program 225 is depicted as operating on computer 200. In various embodiments, computer 200 is a medical professional's computer. In an embodiment, MPMA program 225 operates on computer 200 that is a server providing mammogram evaluations to a number of client devices (e.g., to a number of medical personnel's or physician's computers). In one embodiment, MPMA program 225 resides on computer 300 and receives mammograms (e.g., mammogram image data) from imaging equipment 330 or storage 350. MPMA program 225 provides an evaluation of a current or most recent mammogram using both the current mammogram and a set of prior mammograms associated with a patient. MPMA program 225 may receive and send data to and from computer 300, image database 450 on server 400, storage 250, and other computer devices not depicted within computing environment 100 using network 110.

For training of the deep learning algorithms (e.g., training of the CNN, RF classifier, and modified LSTM), MPMA program 225 can retrieve a large number of mammogram images with known, verified outcomes (e.g., a verified as a normal or an abnormal mammogram by further testing or additional mammograms, biopsies, ultrasounds, etc.) from one or more of image storage database 450, storage 350, or storage 250.

In various embodiments, MPMA program 225 uses a trained CNN and one of a trained RF classifier or a trained, modified LSTM algorithm to evaluate a current mammogram of a patient with a set of previous mammograms of a patient. A CNN can employ a mathematical operation called convolution and consists of an input and an output layer, as well as multiple hidden layers where, in typical applications, the hidden layers of a CNN consist of a series of convolutional layers that convolve with a multiplication or other dot product. In various embodiments, the training of either of the RF classifier or the modified LSTM in MPMA program 225 occurs after the CNN training. As known to one skilled in the art, a LSTM is an artificial recurrent neural network architecture used in deep learning that has feedback connections (e.g., it processes not only single data points or images, but also entire sequences of data or images).

MPMA program 225, after training of the deep learning algorithms, receives a current, unevaluated mammogram of a patient and a set of one or more prior mammograms from the same patient, for example, from one or more of imaging equipment 330 in computer 300, from storage 350, from storage 250, or from image database 450 in server 400. MPMA program 225, using the trained deep learning algorithms (i.e., trained CNN and either the trained RF or modified LSTM), can provide an evaluation of the current mammogram. The result of the evaluation of the current mammogram, for example, as normal or abnormal, may be displayed on UI 260 to a physician.

Storage 250 is depicted in computer 200. Storage 250 may be any known type of storage and may include one or more databases. Storage 250 may store mammograms, meta data or files associated with mammograms, evaluations of mammograms by MPMA program 225, any additional information or data from another source (e.g., reports, ultrasound, biopsies, mammograms, etc.) from imaging equipment 330, database 450, other medical devices, or other computing devices (not depicted) in computer environment 100.

UI 260 provides an interface to access the features and functions of server 400. In some embodiments, UI 260 provides to a user access to MPMA program 225 or to data in storage 250. UI 260 provides display of output and input functions for computer 200. UI 250 enables respective users of computer 200 to receive, view, hear, and respond to input, access applications, display content, and perform available functions. UI 260 may be any type of user interface capable of receiving a user's input to a program or a program's output. For example, UI 260 may be a touch screen display, a high definition display screen, a keyboard, an audio output, an audio recording device with a voice recognition system, etc.

As depicted, computer 300 is a computing device including imaging equipment 330 capable of capturing mammogram images. Computer 300 may be a desktop computer, laptop computer, a tablet computer, or any programmable electronic device capable of including or directly connecting to imaging equipment 330 and communicating with various components and devices within computer environment 100, via network 110. In general, computer 300 represents one or more programmable electronic devices or a combination of programmable electronic devices capable of executing machine-readable program instructions, imaging capabilities, and communicating with computer 200, server 400, and other computing devices not shown within computer environment 100 via a network, such as network 110. Computer 300, as depicted, includes imaging equipment 330, storage 350, and UI 360.

Imaging equipment 330 may be any known type of mammogram x-ray device or imaging device capable of providing mammograms or other medical images. Imaging equipment 330 can be capable of creating high quality images as mammograms using industry standard mammogram procedures. Imaging equipment 330 can capture and store captured images in storage 350. Imaging equipment 330 can be pre-programmed to send images to MPMA program 225 and image database 450.

In some embodiments, a program (not depicted) in computer 300 is includes instructions to retrieve generated images, such as, mammograms from storage 350. Computer 300 may include instructions to retrieve images and send the retrieved images to one or more of MPMA program 225 in computer 200, to image database 450, or to storage 350 when imaging occurs or on a pre-determined time interval, such as, every hour, every day, etc. In some embodiments, imaging equipment 330 is a standalone imaging device automatically sending data, such as, mammogram images and data associated with capturing mammograms over network 110 to one or more of computer 300, server 400 or computer 200. Computer 300 may include internal and external hardware components, depicted in more detail in FIG. 5.

Storage 350 is depicted in computer 300. Storage 350 may be any known type of storage and may include one or more databases. Storage 350 may store mammograms and mammogram metadata (e.g., time taken, resolution, technician, equipment model, etc.) from imaging equipment 330, any additional received evaluations from MPMA program 225, data from server 400, or from other computing devices within computer environment 100. In various embodiments, storage 350 receives, retrieves, and sends data, such as, mammograms or data associated with mammograms to and from imaging equipment 330, UI 360, computer 200, server 400, and other computing devices not depicted in computer environment over network 110.

UI 360 provides an interface to access the features and functions of computer 300. UI 360 enables respective users of computer 300 to receive, view, hear, and respond to input, access applications, display content, and perform available functions on computer 300. In some embodiments, UI 360 provides instructions to imaging equipment 330. UI 360 provides a user of computer 300 with the ability to display data and communicate instructions, data, images, and the like from programs and equipment associated with computer 300, computer 200, server 400 and other computing devices in computer environment 100. UI 360 includes the functions and capabilities of any standard UI, such as UI 260 above.

Server 400 is depicted as including image database 450. In some embodiments, server 130 can be a web server, a mainframe computer, a desktop computer, a laptop computer, a tablet computer, a netbook computer, or any other programmable electronic computing device capable of receiving, sending, and processing data, and communicating with features and functions of computer 200, computer 300, and other computing devices (not shown) within computer environment 100 via network 110. In another embodiment, server 400 represents a computing system utilizing clustered computers and components (e.g., database server computers, application server computers, etc.) that act as a single pool of seamless resources when accessed within distributed data processing environment 100. Server 400 may include internal and external hardware components, as depicted in more detail and described in FIG. 5.

Image database 450, depicted as residing in server 400, is a data repository. Image database 450 can be one or more databases containing mammogram images, data associated with each mammogram image, such as, a mammogram date taken, the type of equipment used for the mammogram (e.g., make, model, manufacturer, type of images, three dimensional mammograms, image resolution, etc.), image evaluations, technician, and any other data provided to image database 450. In various embodiments, image database 450 retrieves, sends, and stores data from and to computer 200, computer 300, and other computing devices not depicted in FIG. 1.

Figure 2A:
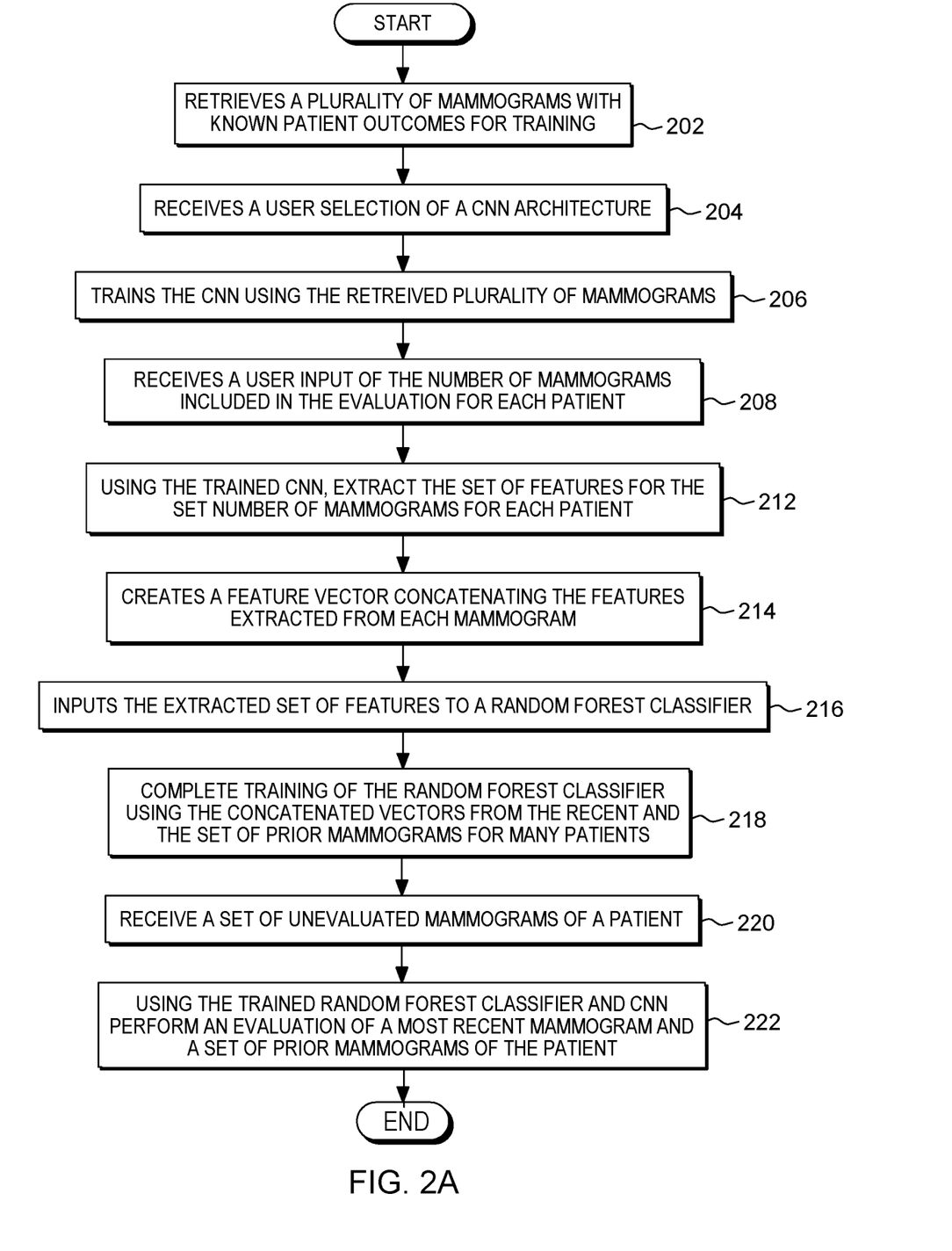
FIG. 2A is a flow chart diagram depicting operational steps for the multiple prior mammogram assessment program using a convolutional neural network with random forest classifiers, in accordance with at least one embodiment of the invention.

FIG. 2 is a flow chart diagram depicting operational steps for training and using a trained MPMA program 225 when MPMA program 225 includes a CNN and a RF classifier, in accordance with at least one embodiment of the invention. The trained MPMA program 225 provides an output that is an outcome of the evaluation of the current or new mammogram of the patient using a number of prior mammograms of a patient and the current mammogram. Steps 202 through 206 discuss a method to train a CNN for use in MPMA program 225. Steps 208 through 220 discuss, in detail, the training of the RF classifier using a most recent mammogram of a patient and a set of prior mammograms of the patient. In training and after training, the RF classifier uses the features extracted by the trained CNN for each mammogram (e.g., the features extracted for each prior mammogram and the most recent mammogram of a patient) as an input to the RF classifier.

In step 202, MPMA program 225 retrieves a plurality of mammograms with known patient outcomes from one or more of image database 450, storage 350 in computer 300, or storage 250 in computer 200 over network 110. The plurality of mammograms are taken from a large group of patients who have provided a written consent allowing the use of mammograms and mammogram data to develop MPMA program 225.

For training of the various deep learning algorithms (e.g., a CNN, a random forest classifier, or a modified LSTM), the prior evaluation of each mammogram of the plurality of retrieved mammograms is verified as a correct evaluation (e.g., by further testing, biopsies, by later mammograms, etc.). The plurality of mammograms with known outcomes include many sets of one or more mammograms from the same patient and in some instances, may include only a single mammogram for some patients. The plurality of mammograms retrieved from image database 450 or another source. In various embodiments, the retrieved mammograms include information, such as, a date a mammogram was taken, the equipment the mammogram was taken on, image resolution of the mammogram, the nurse or medical technician who captured the mammogram, the type of view, the area captured, captured structural elements (e.g., muscles, etc.), which breast is captured, and other similar information relating to the mammogram. The information associated with each mammogram may be embedded in the mammogram image data (e.g., metadata), on the image, or in a file associated with mammogram.

In step 204, MPMA program 225 receives a user selection of a CNN architecture. For example, with a selected CNN architecture, a set of features can be extracted from each retrieved mammogram from the plurality of mammograms with a verified previous evaluation. The number of features extracted can be variable and dependent on the architecture of the CNN. For example, the set of features can be 128. In this case, the size of the feature vector, $F_c$, of the current mammogram image will be 1×128.

In step 206, MPMA program 225 trains the CNN using the plurality of mammograms retrieved by MPMA program 225. The training of the CNN occurs by evaluating each of the plurality of mammograms with known outcomes using conventional deep learning algorithm training methods. In various embodiments, the training of the CNN occurs when MPMA program 225 includes the CNN.

In one embodiment, the CNN is a separate program from MPMA program 225 while under training. In this case, the CNN is trained separate from MPMA program 225 and then, the trained CNN is incorporated into MPMA program 225 (e.g., the code and instructions of the trained CNN is added to MPMA program 225).

The CNN evaluates only a single mammogram, based the set of features extracted from the image. The CNN does not include any prior mammograms in training or in the evaluation of mammogram. A final layer or a set of layers can be used to perform a prediction based on the extracted set of features. The training of the CNN occurs using the retrieved plurality of mammograms with known outcomes. Based, at least in part, on a set extracted features of the mammogram, a final layer(s) of the CNN could provide an evaluation of a single, current, mammogram during training. The training of the CNN compares each CNN outcome to the known outcome of the mammogram using conventional deep learning algorithm training methodologies.

In step 208, MPMA program 225 receives a user selection of a number of mammograms of each patient to be included in the evaluation of a mammogram of the patient by MPMA program 225 using the RF classifier. The RF classifier in MPMA program 225 requires a fixed input size. The number of mammograms utilized in MPMA program 225 using the trained CNN and a RF classifier can be set by a user. The number of mammograms includes the current mammogram for evaluation and a set of prior mammograms of each patient.

In step 212, using the trained CNN, MPMA program 225 extracts the set of features for each mammogram of the set of mammograms for each patient. For the training of the RF classifier, the trained CNN inputs the set of features, for example, a set of 128 features for each mammogram of the number of mammograms for each patient. The trained CNN provides the set of features for a current mammogram being evaluated (i.e., with a known outcome) and a set of features for each of the prior mammograms for the patient to the RF classifier. The total number of mammograms (e.g., the current mammogram with the set of prior mammograms) matches the number of mammograms defined for the RF classifier in step 208.

Figure 2B:
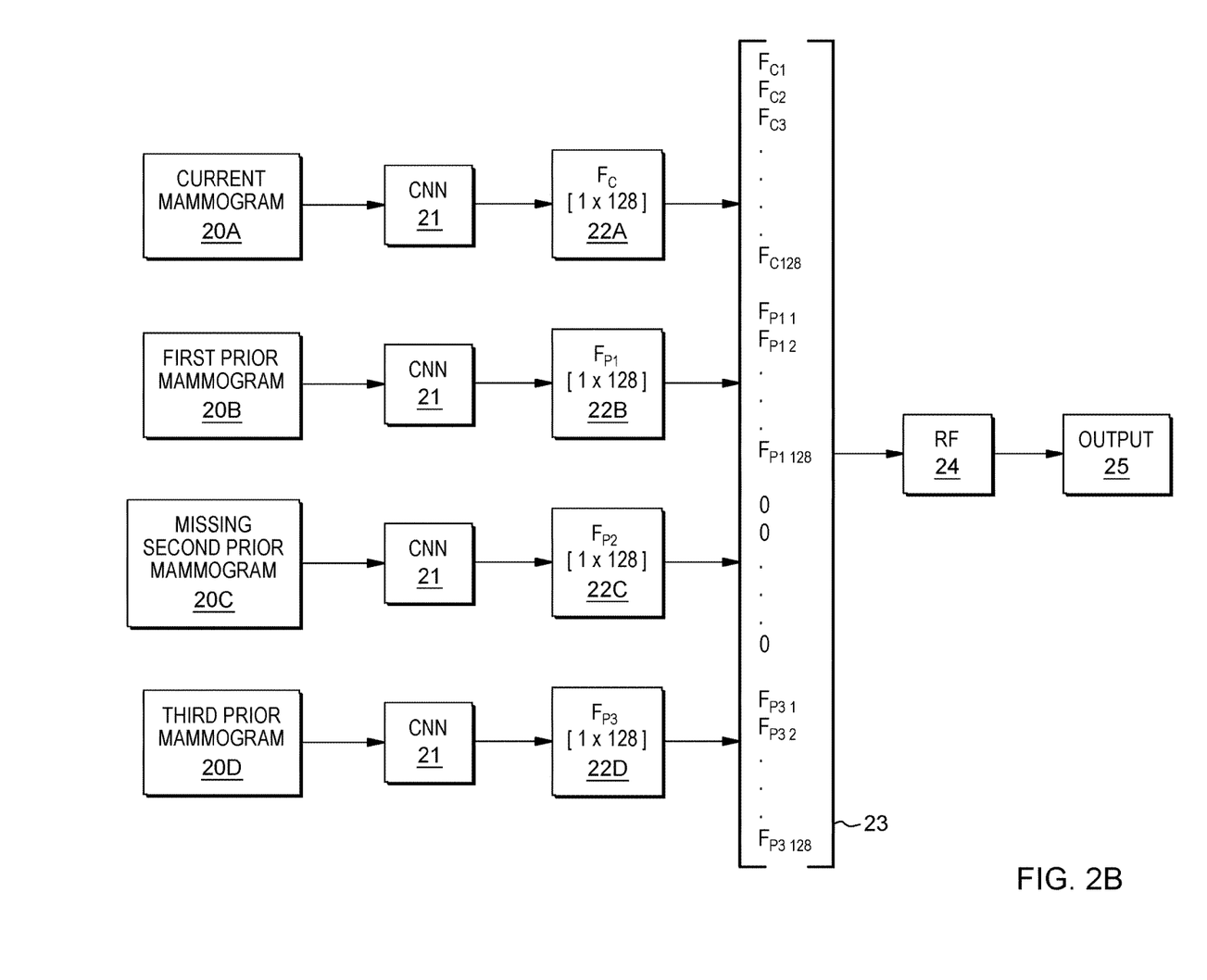
FIG. 2B is a block diagram illustrating multiple prior mammogram assessment program 225 using a convolutional neural network with a random forest classifier, in accordance with at least one embodiment of the invention.

In the case of missing second prior mammogram 20C, the second prior mammogram of the patient was not performed, or the mammogram data is not available. In this case, MPMA program 225 loads the feature vector, $F_{p2}$, for missing second prior mammogram 20C with zeros.

In step 214, MPMA program 225 creates a feature vector concatenating the set of features extracted from each mammogram. From the plurality of mammograms with known outcomes, MPMA program 225 creates a feature vector using the set of features extracted by the CNN for the current mammogram being evaluated and for each of the prior mammograms of a patient. In an example illustrated in FIG. 2B, the set of features, $F_c$ 22A, for current mammogram 20A, form elements $Fc_1$, $Fc_2$, $Fc_3$ to $Fc_{128}$ in concatenated features 23 (a feature vector).

In some cases, a patient may not have the number of mammograms defined in step 208. When the number of mammograms for a patient does not meet the defined number of mammograms to be used by the RF classifier, MPMA program 225 fills the set of feature vectors with zeros (e.g., MPMA program 225 has filled the set of features with zeros in step 208). In this way, the required number of mammograms defined in the RF classifier can be maintained by MPMA program 225 even when a patient has not had the required number of mammograms. The second prior mammogram 20C of FIG. 2B depicts an example of a patient with a missing mammogram where the feature vector $F_{P2}$ is filled with zeros (not depicted in FIG. 2B) and the associated concatenated features are zeros.

In step 216, MPMA program 225 inputs the extracted set of features to the RF classifier for each mammogram of a patient. MPMA program 225 inputs the set of features and the concatenated features for the current mammogram for each prior mammogram of a patient (e.g., from the set of mammograms with known outcomes). The concatenated features can be input into the RF classifier. MPMA program 225 uses the concatenated features for training the RF classifier using conventional deep learning training methods.

In step 218, MPMA program 225 completes the training of the random forest classifier using the concatenated features from the current mammogram and the set of prior mammograms for each patients of a large number of patients from the plurality of mammograms with known outcomes. As depicted in FIG. 2B, when the training of the random forest classifier is complete, output 25 of RF 24 should match the known outcome of current mammogram 20A.

In step 220, MPMA program 225 receives a current, unevaluated mammogram for evaluation and a set of prior mammograms of a patient. For example, after training the CNN and training the RF classifier, MPMA program 225 may receive, from computer 300, a current mammogram of a patient captured by imaging equipment 330 and a set of prior mammograms for the same patient from storage 350.

In step 222, MPMA program 225 using the trained RF classifier and trained CNN, performs an evaluation of the current mammogram of a patient based, at least in part, on the set of prior mammograms of the patient. Using the trained deep learning algorithms with the current mammogram and one or more prior mammograms of the patient, MPMA program 225 may provide an evaluation or prediction of the patient's current mammogram and the program ends. For example, MPMA program 225 may provide a binary output for output 25. Output 25 can be a binary output such as "normal" or "recall" where recall indicates that further evaluation and/or monitoring of the patient is required (e.g., perform another mammogram in 6 months or perform a biopsy of identified abnormal tissue). In some cases, the binary output for output 25 may be "abnormal" or "normal" where "abnormal" also may indicate further testing or another screening examination of any identified abnormalities such as, a cluster of malignant microcalcification in the examined tissue. In other embodiments, MPMA program 225 output 25 is one or more of a descriptive phrase, graph, or numerical output (e.g., a percent of risk, a percent normal tissue, etc.).

FIG. 2B is a block diagram illustrating MPMA program 225 using CNN 21 with RF classifier 24, in accordance with at least one embodiment of the invention. As depicted, FIG. 2B includes CNN 21, feature vectors, Fc 22A, $Fp_1$ 22B, $Fp_2$ 22C, $Fp_3$ 22D, current mammogram 20A, first prior mammogram 20B, missing second prior mammogram 20C, third prior mammogram 20D, and concatenating features 23 along with RF 24 and output 25. Concatenating features 23 is a feature vector from the set of features (e.g., $F_C$ 22A-$F_{P3}$ 22D) determined by CNN 21. CNN 21 and RF 24 are trained, for example, as discussed with respect to steps 202 to 206 of FIG. 2A. In FIG. 2B, MPMA program 225 has received a set of mammograms associated with a patient in order for MPMA program 225 to provide an evaluation for output 25 of current mammogram 20A. The set of mammograms, as depicted, include current mammogram 20A, first prior mammogram 20B, missing second prior mammogram 20C, and third prior mammogram 20D. As previously described, RF 24, requires a fixed input size, so since the second prior mammogram is missing, MPMA program 225 will create a feature vector filled with zeros for missing second prior mammogram 20C. MPMA program 225 as depicted in FIG. 2B, provides output 25 of an evaluation of the current mammogram based, at least in, part on a set of prior mammograms for the same patient.

Figure 3:
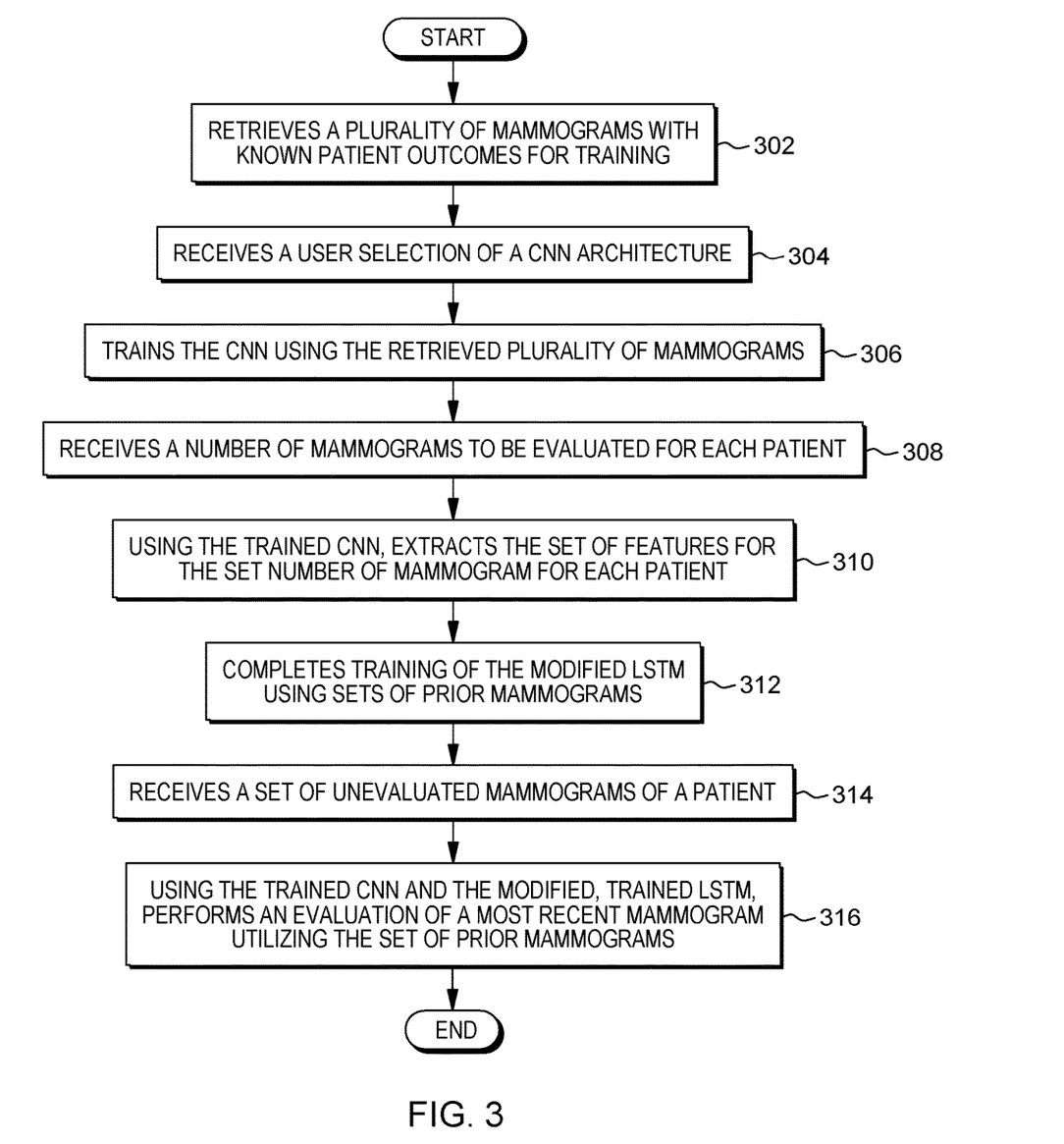
FIG. 3 is a flow chart diagram depicting operational steps for the multiple prior mammogram assessment program using a convolutional neural network with a modified long short-term memory algorithm, in accordance with at least one embodiment of the invention.

FIG. 3 is a flow chart diagram depicting operational steps for MPMA program 225 using a trained CNN with a modified LSTM, in accordance with at least one embodiment of the invention. After completing training of the CNN and the modified LSTM, MPMA program 225 evaluates a current mammogram of a patient based, at least in part, on a set of prior mammograms of the patient.

In step 302, MPMA program 225 retrieves a plurality of mammograms with known patient outcomes for training the CNN and the modified LSTM. In some embodiments, MPMA program 225 retrieves the plurality of mammograms from image database 450 in server 400 using network 110. In other embodiments, MPMA program 225 retrieves the plurality of mammograms from one or more of storage 350 in computer 300, storage 250 in computer 200, another computer system storage or database in computer environment 100.

In step 304, MPMA program 225 receives a user selection of a CNN architecture. As discussed in detail with previously with reference to step 204 of FIG. 2, using the selected CNN architecture, a set of features can be extracted from each retrieved mammogram from the plurality of mammograms with a verified previous evaluation.

In step 306, as previously discussed in detail with reference to step 206 in FIG. 2, MPMA program 225 trains the CNN using the plurality of mammograms retrieved by MPMA program 225. Using conventional methods, the training of the CNN occurs by evaluating each of the plurality of mammograms with known outcomes.

In step 308, MPMA program 225 receives a user selection of a number of mammograms to be evaluated in MPMA program 225. As known to one skilled in the art, a LSTM algorithm, unlike the RF classifier, can handle a variable number of inputs or mammograms. If a prior mammogram is missing when input into MPMA program 225 when using the modified LSTM, the program will not need to generate an input (e.g., zeros) for the missing mammogram. The number of mammograms includes the current mammogram for evaluation and a set of prior mammograms of each patient. For training, the current mammogram and the set of prior mammograms for training are from the plurality of mammograms with known outcomes.

In step 310, as previously discussed in detail with reference to step 212, using the trained CNN, MPMA program 225 extracts the set of features for each mammogram of the number of mammograms for each patient. The extracted set of features from each mammogram in the plurality of mammograms with known outcomes can be input by MPMA program 225 into the modified LSTM for training of the modified LSTM.

In step 312, MPMA program 225 completes the training of the modified LSTM using the sets of prior mammograms of a large number of patients. Using the sets of mammograms where each set of mammograms is associated with one patient. Each mammogram evaluated has a verified, known outcome for training the modified LSTM (e.g., the mammograms used in training are from the plurality of mammograms with known outcomes).

During training the modified LSTM, the modified LSTM includes the number of mammograms, if available, as defined in step 308, for a patient. As known to one skilled in the art, an LSTM sequentially processes each received input in a stepwise approach. The input to the modified LSTM, at each sequence step or time point, is a mammogram where the oldest prior mammogram is input first in the modified LSTM and the current mammogram is input last to the modified LSTM in MPMA program 225.

The evaluation of a most recent mammogram of the set of mammograms of the patient is based, at least in part, on the most recent mammograms and the remaining mammograms in the set of mammograms of the patient. In training, the outcome of MPMA program 225 using the modified LSTM can be compared to an outcome of the most recent mammogram of the patient that has been verified (e.g., by later mammograms, ultrasounds, etc.).

As opposed to a conventional LSTM, the modified LSTM assigns different weights to different prior mammograms based, at least in part, on an image quality of each mammogram of the patient and on the time elapsed from the most recent mammogram under evaluation. For example, a mammogram with higher image quality or a mammogram that is more recent (e.g., with less time elapsed from the mammogram under evaluation than an older mammogram of the patient) can be given more weight in the modified LSTM.

The modified LSTM algorithm considers different features when assessing image quality. For example, when evaluating image quality, the modified LSTM considers a combination of positioning and image clarity. Breast positioning can determine if the appropriate landmarks or structural elements (e.g., such as the pectoral muscle) are present in the image. Image clarity may determine an amount of blur in the image caused by movement where images with blur or higher levels of blur would be considered low quality images. Other factors included by the modified LSTM in weighting image quality may be the level of contrast in the mammogram. Older mammogram equipment or low compression of the breast during testing may cause low contrast images. In the modified LSTM, mammograms with better image quality can be given more weight than mammograms with lower image quality.

An example of a set of equations for a modified LSTM includes $f_t = \sigma(W_{fh}*h^{t-1} + W_{fx}*x^t + W_{fd}*\delta^t + W_{fq}*q^t + b_f)$ as a first equation, $i_t = \sigma(W_{ih}*h^{t-1} + W_{ix}*x^t + W_{id}*\delta^t + W_{iq}*q^t + b_i)$ as a second equation, $o_t = \sigma(W_{oh}*h^{t-1} + W_{ox}*x^t + W_{od}*\delta^t + W_{oq}*q^t + b_o)$ as a third equation, $c_t = \sigma(W_{ch}*h^{t-1} + W_{cx}*x^t + W_{cd}*\delta^t + W_{cq}*q^t + b_c)$ as a fourth equation, $h_t = f_t*h_{t-1} + i_t*c_t$ as a fifth equation, and $y_t = o_t*\tanh(h_t)$ as a sixth equation and where $x^t$ is the input vector, $c_t$ is the long-term state, $h_t$ is the short-term state, $f_t$ is the forget gate, $i_t$ is the input gate, $o_t$ is the output gate, $\delta^t$ is the time difference between the prior at time t and the current exam, $q_t$ is the quality measure of the exam at time t, and $y_t$ is the output.

Additionally, $W_{fh}$, $W_{ih}$, $W_{oh}$, and $W_{ch}$ are the weight matrices of each of the four layers for their connection to the previous short-term state $h^t$, $W_{fx}$, $W_{ix}$, $W_{ox}$, and $W_{cx}$ are the weight matrices of each of the four layers for their connection to the input vector $x^t$, $W_{fd}$, $W_{id}$, $W_{od}$, and $W_{cd}$ are the weight matrices of each of the four layers for their connection to the time difference between the prior at time t and the current exam $\delta^t$, $W_{fg}$, $W_{ig}$, $W_{og}$, and $W_{cg}$ are the weight matrices of each of the four layers for their connection to the quality measure of the exam at time t, $q^t$, and $b_f$, $b_i$, $b_o$, and $b_c$ are the bias terms for each of the four layers.

The new elements in the modified LSTM algorithm depicted in the set of equations above include, at least, the addition of $q_t$, a measurement of each mammogram's image quality, and $\delta_t$, a time elapsed from the most recent mammogram under evaluation, $W_{fd}$, $W_{id}$, $W_{od}$, and $W_{cd}$, the weight matrices associated with the measure of image quality, $W_{iq}$, $W_{fq}$, $W_{iq}$, and $W_{cq}$, the weight matrices associated with the time elapsed from the most recent mammogram under evaluation. MPMA program 225 with the inclusion of a measure of image quality of a mammogram and a measure of the time elapsed from performing the most recent mammogram to the time of each prior mammogram is created (e.g., when the mammogram is performed) as weighting factors for each prior mammogram of the patient provides an improvement in outcomes or evaluations of a most recent mammogram over an outcome generated by a conventional LSTM algorithm. As previously stated, using a conventional LSTM would not include a consideration of previous mammograms, image quality of each mammogram, and a time elapsed from the most recent mammogram in an evaluation the most recent mammogram.

In some embodiments, MPMA program 225 can be modified to detect asymmetry by modifications to the program to include views from both a left side and a right side of the patient (e.g., a left breast and a right breast). The modifications to include mammograms from both sides of the patient can incorporated in both the training of MPMA program 225 (e.g., in the training of the CNN, RF classifier, and/or the modified LSTM) and in evaluations of a current mammogram after training. In these embodiments, MPMA program 225 can be adjusted so that the input has two channels rather than just one channel.

In step 314, MPMA program 225 receives a most recent mammogram and a set of prior mammograms of a patient. In various embodiments, MPMA program 225 receives a most recent or current mammogram of the patient that has not been evaluated before from computer 300 over network 110. Each mammogram of the set of prior mammograms of the patient can include a time stamp or meta data identifying a time taken and/or a model or date of manufacture of the equipment used to capture the mammogram. In some examples, the data on time taken and equipment used may be in a separate file sent to MPMA program 225 or included as meta data with the mammogram.

In step 316, MPMA program 225 using the trained CNN and modified LSTM evaluates the most recent mammogram based, at least in part, on the set of prior mammograms of the patient. In this case, MPMA program 225 factors the image quality of each mammogram and the time elapsed from the most recent mammogram for each of the set of prior mammograms in the modified LSTM of MPMA program 225. As previously discussed, the evaluation of the most recent mammogram may be normal or abnormal but is not limited to these specific evaluations or outcomes (e.g., may be a numerical output, a graphical output, etc.).

In one study of a number use cases with known outcomes, a comparison of accuracy of the outcomes (e.g., predictions) of the conventional method of evaluation of a single mammogram using a trained CNN alone was compared to the method using a trained CNN combined with a one of a RF classifier or a modified LSTM trained with a number of prior mammograms of the patient and the current mammogram of the patient. In this example, MPMA program 225 combines one of a trained RF classifier or a trained modified LSTM for evaluation of a current mammogram. In this study, the trained CNN combined with the trained RF classifier or the trained modified LSTM provided better results than the conventionally trained CNN alone.

In this example, the study compares the receiver operating characteristic (ROC) curve analysis of the outcomes of a conventionally trained CNN (e.g., provides on outcome of a single mammogram after training) and the method of MPMA program 225 using a conventionally trained CNN with one of a trained RF classifier or a trained modified LSTM and a set of a patient's mammograms. For example, the area under the ROC curve predicting whether a mammogram contains cancer for the modified LSTM in MPMA program 225 was 0.946, while the area under the ROC curve using only a conventionally trained CNN evaluating a single mammogram is 0.866. Using MPMA program 225 with a trained CNN and a trained RF classifier in MPMA program 225 resulted in an area under the curve of 0.906.

The specificity at a sensitivity of 0.90% (e.g., related to the recall rate or a missed cancer diagnosis) for a single mammogram evaluated using a conventional CNN was seen as 0.671 while the specificity at a sensitivity of 90% for MPMA program 225 with the RF classifier was 0.809 and the MPMA program 225 with the modified LSTM was 0.871. Based the above results, MPMA program 225 using either of an RF classifier or a modified LSTM when trained with multiple prior mammograms and a trained CNN demonstrates an improvement in both the specificity and the area under the ROC curve over a conventional trained CNN that evaluates only a current mammogram.

Figure 4:
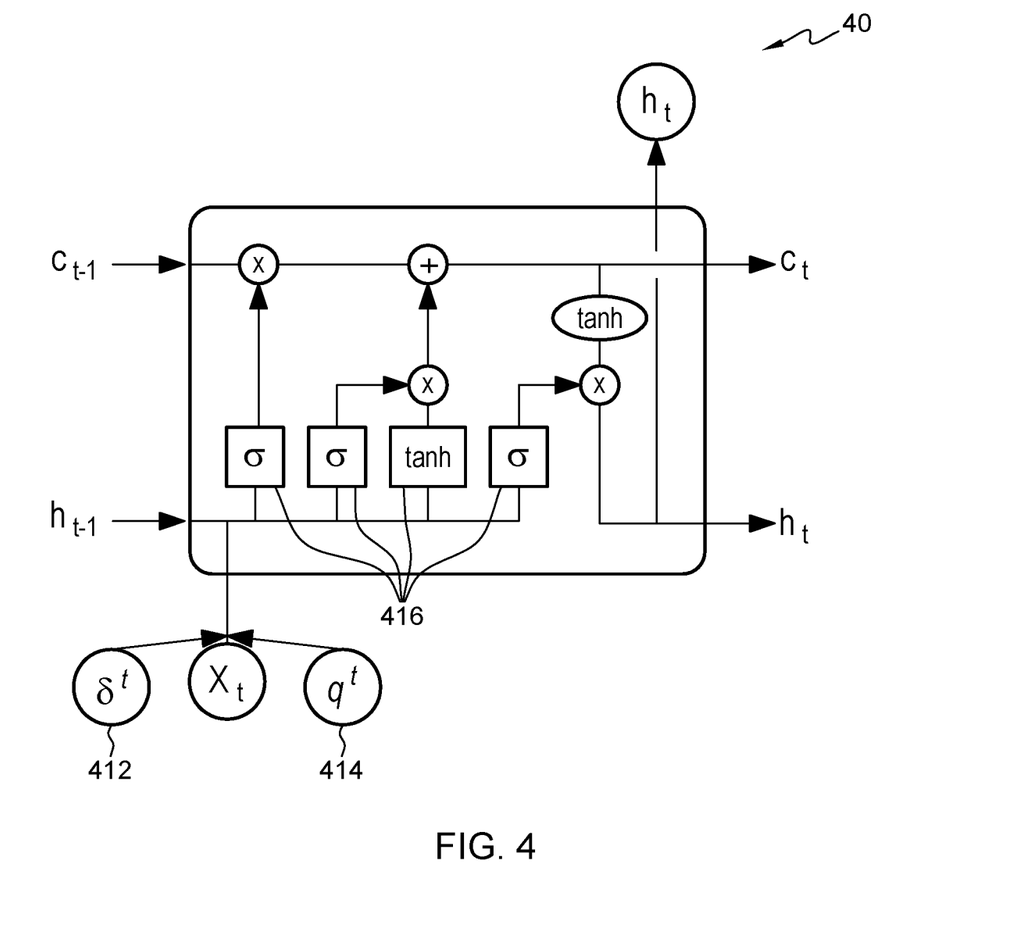
FIG. 4 is an example of a program flow chart for a repeating module in the modified LSTM algorithm for evaluating a mammogram using multiple prior mammograms, in accordance with at least one embodiment of the invention.

FIG. 4 is an example of a program flow chart for repeating module 40 of the modified LSTM algorithm, in accordance with at least one embodiment of the invention. As known to one skilled in the art, repeating module 40 in the modified LSTM in includes four interacting layers (e.g., the forget gate controlling which parts of the long-term state should be erased, the input gate controlling which parts of the long-term state should be updated, the output gate controlling which parts of the long-term state should be output at this time step, and the long-term state). As depicted, FIG. 4 illustrates repeating module 40 at a time, t. Stepwise, over time, each repeating module 40 receives additional inputs causing the long-term state to evolve as more and more inputs are received. Repeating module 40 can be also be known as a cell in the modified LSTM. The input to the LSTM model and the input to each repeating module 40 at each time point is a mammogram. The indexing, such as t−1, t, t+2, etc. keeps track of the prior mammograms which have been fed into the model sequentially. The prior mammograms are fed into the model sequentially, by date, and then, the current mammogram is fed in last.

Repeating module 40 is an example of a step in the modified LSTM sequence occurring at time, t, where the next repeating module in the sequence (not depicted in FIG. 4) occurs at a time, t+1. The next sequence of repeating module 40 at time, t+1, receives the outputs and learned weights from repeating module 40 at time, t, as inputs. Similarly, repeating module 410 can receive inputs from a previous repeating module 40 (e.g., previously occurring at time, t−1).

Repeating module 40, as depicted in FIG. 4, includes two new or novel elements not used in a repeating module of a traditional LSTM. As depicted in FIG. 4, repeating module 40 includes additional factors $\delta^t$ 412 and $q^t$ 414. $\delta^t$ 412 provides a weighting factor for a time elapsed from a current mammogram under evaluation and $q^t$ 414 provides a weighting factor for image quality. As known to one skilled in the art, each of 416 represents a layer in the modified LSTM, while $x_t$, $\sigma$, $h_t$, $c_t$, tanh, are standard variables as described above with reference to equation (1) and x, +, and tanh pointwise operands (e.g., ops). As depicted, FIG. 4 is one example of a repeating module in the modified LSTM of MPMA program 225 when a modified LSTM is incorporated into MPMA program 225.

While embodiments of the present invention discuss MPMA program 225 as a program using trained deep learning algorithms to evaluate a current or most recent mammogram, in other embodiments, MPMA program 225 can receive examination screening images related to other types of medical imaging procedures such as, cat scans or ultrasounds, for diagnosing other patient conditions. For example, images from ultrasounds, colonoscopies, lung tissue x-rays, prostrate images, or similar patient diagnostic images can be evaluated using MPMA program 225 when trained with a same type of image (e.g., evaluate a current colonoscopy based on training using a plurality of colonoscopies with known outcomes). It is to be understood that while embodiments of the present invention may refer to the images as mammograms, MPMA program 225 is not limited to evaluations associated to mammograms but, MPMA program 225 can be used to any number of other types of diagnostic images for patients (e.g., cat scans, ultrasounds, lung x-rays, etc.). In an embodiment, some modification of MPMA program 225 occur when MPMA program is applied with other types of images.

Figure 5:
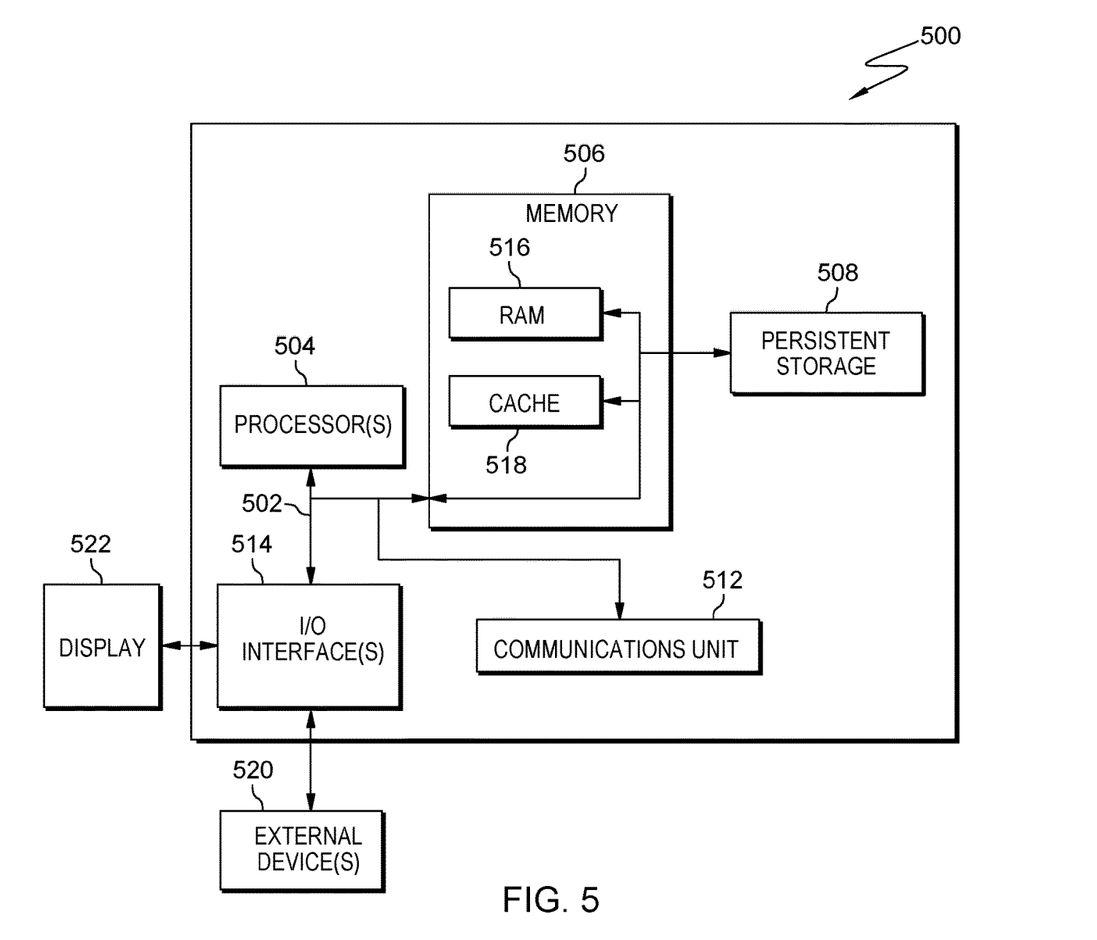
FIG. 5 is a block diagram depicting components of a computer system suitable for executing the multiple prior mammogram assessment program, in accordance with at least one embodiment of the invention.

FIG. 5 is a block diagram depicting components of a computer system 500 suitable for MPMA program 225, in accordance with at least one embodiment of the invention. FIG. 5 displays the computer system 500, one or more processor(s) 504 (including one or more computer processors or central processor units), a communications fabric 502, a memory 506 including, a RAM 516, and a cache 518, a persistent storage 508, a communications unit 512, I/O interfaces 514, a display 522, and external devices 520. It should be appreciated that FIG. 5 provides only an illustration of one embodiment and does not imply any limitations with regard to the environments in which different embodiments may be implemented. Many modifications to the depicted environment may be made.

As depicted, the computer system 500 operates over the communications fabric 502, which provides communications between the computer processor(s) 504, memory 506, persistent storage 508, communications unit 512, and input/output (I/O) interface(s) 514. The communications fabric 502 may be implemented with an architecture suitable for passing data or control information between the processors 504 (e.g., microprocessors, communications processors, and network processors), the memory 506, the external devices 520, and any other hardware components within a system. For example, the communications fabric 502 may be implemented with one or more buses.

The memory 506 and persistent storage 508 are computer readable storage media. In the depicted embodiment, the memory 506 comprises a random-access memory (RAM) 516 and a cache 518. In general, the memory 506 may comprise any suitable volatile or non-volatile one or more computer readable storage media.

Program instructions for MPMA program 225 may be stored in the persistent storage 508, or more generally, any computer readable storage media, for execution by one or more of the respective computer processors 504 via one or more memories of the memory 506. In an embodiment, program instructions for MPMA program 225 may be stored in memory 506. The persistent storage 508 may be a magnetic hard disk drive, a solid-state disk drive, a semiconductor storage device, read only memory (ROM), electronically erasable programmable read-only memory (EEPROM), flash memory, or any other computer readable storage media that is capable of storing program instruction or digital information.

The media used by the persistent storage 508 may also be removable. For example, a removable hard drive may be used for persistent storage 508. Other examples include optical and magnetic disks, thumb drives, and smart cards that are inserted into a drive for transfer onto another computer readable storage medium that is also part of the persistent storage 508.

The communications unit 512, in these examples, provides for communications with other data processing systems or devices. In these examples, the communications unit 512 may comprise one or more network interface cards. The communications unit 512 may provide communications through the use of either or both physical and wireless communications links. In the context of some embodiments of the present invention, the source of the various input data may be physically remote to the computer system 500 such that the input data may be received, and the output similarly transmitted via the communications unit 512.

The I/O interface(s) 514 allow for input and output of data with other devices that may operate in conjunction with the computer system 500. For example, the I/O interface 514 may provide a connection to the external devices 520, which may be as a keyboard, keypad, a touch screen, or other suitable input devices. External devices 520 may also include portable computer readable storage media, for example thumb drives, portable optical or magnetic disks, and memory cards. Software and data used to practice embodiments of the present invention may be stored on such portable computer readable storage media and may be loaded onto the persistent storage 508 via the I/O interface(s) 514. The I/O interface(s) 514 may similarly connect to a display 522. The display 522 provides a mechanism to display data to a user and may be, for example, a computer monitor.

The present invention may be a system, a method, and/or a computer program product at any possible technical detail level of integration. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disk read-only memory (CD-ROM), a digital versatile disk (DVD), a memory stick, a floppy disk, a mechanically encoded device such as punchcards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adaptor card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, though the Internet using an Internet Service Provider). In some embodiments, electronic circuitry including, for example programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general-purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram blocks or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of computer program instructions, which comprises one or more executable instructions for implementing the specified logical function(s). In some alternative implementations, the functions noted in the block may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

What is claimed is:

1. A computer program product comprising:
   one or more computer readable storage media and program instructions stored on the one or more computer readable storage media, the program instructions executable by a processor, the program instructions comprising instructions for:
   extracting, by one or more computer processors, by a trained convolutional neural network, a set of features from each mammogram of a plurality of mammograms with known outcomes, further comprises training one of a random forest classifier or a modified long-short term memory algorithm, wherein training the modified long-short term algorithm includes providing one or more weighting factors associated with each mammogram of the set of mammograms of each patient from the plurality of patients;
   receiving, by one or more computer processors, a first set of mammograms for a first patient wherein, the first set of mammograms of the first patient includes an unevaluated mammogram of the first patient and a set of prior mammograms of the first patient;
   extracting, by one or more computer processors, by the trained convolutional neural network, the set of features from each mammogram of the first set of mammograms of the first patient; and performing, by one or more computer processors, an evaluation of the unevaluated mammogram of the first patient using the trained convolutional neural network and a deep learning algorithm of the one or more trained deep learning algorithms based, at least in part, on the set of prior mammograms of the first patient.

2. The computer program product of claim 1, further comprises providing an output of the evaluation of the unevaluated mammogram of the first patient wherein, the output includes one or more of a graphical output, a numerical output, a written output, or a binary outcome.

3. The computer program product of claim 2, wherein the binary outcome includes one of normal or abnormal.

4. The computer program product of claim 1, wherein an image quality of each mammogram of the set of mammograms of each patient is a weighting factor of the one or more weighting factors associated with each mammogram of the set of mammograms of each patient.

5. The computer program product of claim 1, wherein training the modified long-short term algorithm includes a weighting factor associated with a time elapsed from a current mammogram being evaluated to each prior mammogram in the set of mammograms of each patient wherein, a more recent mammogram in the set of mammograms with less time elapsed from the current mammogram being evaluated is given more weight than an older mammogram.

6. The computer program product of claim 1, wherein training the training the random forest classifier includes using the trained convolutional neural network, further comprises:

receiving, by one or more computer processors, the first set of mammograms of the first patient wherein, the first set of mammograms of the first patient includes the unevaluated mammogram of the first patient and the set of prior mammograms of the first patient;

extracting, by one or more computer processors, by the trained convolutional neural network, the set of features from each mammogram of the first set of mammograms of the first patient; and performing, by one or more computer processors, the evaluation of the unevaluated mammogram of the first patient using the trained random forest classifier based, at least in part, on the set of prior mammograms of the first patient.

7. The computer program product of claim 1, wherein training the random forest classifier further comprises:

receiving, by one or more computer processors, a user input of a number of mammograms needed for the set of mammograms of each patient of the plurality of patients in the training of the random forest classifier;

creating, by one or more computer processors, a feature vector concatenating each feature of the set of features from each mammogram of the plurality of mammograms with the known outcomes;

determining, by one or more computer processors, that one or more mammograms of the number of mammograms needed for the set of mammograms of each patient of the plurality of patients in the training of the random forest classifier is missing; and inputting, by one or more computer processors, zeros for each feature of the set of features associated with the one or more missing mammograms.

8. A computer system comprising:
one or more computer processors;
one or more computer readable storage media;
program instructions stored on the one or more computer readable storage media for execution by at least one of the one or more processors, the program instructions comprising instructions to perform:

extracting, by one or more computer processors, by a trained convolutional neural network, a set of features from each mammogram of a plurality of mammograms with known outcomes;

training, by one or more computer processors, one or more deep learning algorithms based, at least in part, on using the set of features from each mammogram of a set of mammograms of each patient of a plurality of patients from the plurality of mammograms with the known outcomes, further comprises training one of a random forest classifier or a modified long-short term memory algorithm, wherein training the modified long-short term algorithm includes providing one or more weighting factors associated with each mammogram of the set of mammograms of each patient;

receiving, by one or more computer processors, a first set of mammograms for a first patient wherein, the first set of mammograms includes an unevaluated mammogram of the first patient and a set of prior mammograms of the first patient;

extracting, by one or more computer processors, by the trained convolutional neural network, the set of features from each mammogram of the first set of mammograms of the first patient; and performing, by one or more computer processors, an evaluation of the unevaluated mammogram of the first patient using the trained convolutional neural network and a trained deep learning algorithm of the one or more trained deep learning algorithms based, at least in part, on the set of prior mammograms of the first patient.

9. The computer system of claim 8, wherein an image quality of each mammogram of the set of mammograms of each patient is a weighting factor of the one or more weighting factors associated with each mammogram of the set of mammograms of each patient.

10. The computer system of claim 8, wherein training the random forest classifier further comprises:

receiving, by one or more computer processors, a user input of a number of mammograms needed for the set of mammograms of each patient of the plurality of patients in the training of the random forest classifier;

creating, by one or more computer processors, a feature vector concatenating each feature of the set of features from each mammogram of the plurality of mammograms with the known outcomes;

determining, by one or more computer processors, that one or more mammograms of the number of mammograms needed for the set of mammograms of each patient of the plurality of patients in the training of the random forest classifier is missing; and inputting, by one or more computer processors, zeros for each feature of the set of features associated with the one or more missing mammograms.

11. The computer system of claim 8, wherein the weighting factor is associated with a time elapsed from a current mammogram being evaluated to each prior mammogram in the set of mammograms of each patient wherein, a more recent mammogram in the set of mammograms with less time elapsed from the current mammogram being evaluated is given more weight than an older mammogram.

12. The computer program product of claim 1, wherein training the modified long-short term algorithm can be modified to detect asymmetry by modifications to the program to include mammogram views from both a left side and a right side of each patient of the plurality of patients.

* * * * *